(12) United States Patent
Manjeshwar

(10) Patent No.: US 7,983,735 B2
(45) Date of Patent: Jul. 19, 2011

(54) SIMULATION OF NUCLEAR MEDICAL IMAGING

(75) Inventor: Ravindra Mohan Manjeshwar, Guilderland, NY (US)

(73) Assignee: General Electric Company, Niskayuna, NY (US)

( * ) Notice: Subject to any disclaimer, the term of this patent is extended or adjusted under 35 U.S.C. 154(b) by 2295 days.

(21) Appl. No.: 10/413,838

(22) Filed: Apr. 15, 2003

(65) Prior Publication Data
US 2004/0210132 A1  Oct. 21, 2004

(51) Int. Cl.
*A61B 5/05* (2006.01)
(52) U.S. Cl. ......... 600/436; 600/301; 600/424; 600/437
(58) Field of Classification Search ................... 600/416, 600/436, 409, 410
See application file for complete search history.

(56) References Cited

U.S. PATENT DOCUMENTS

| | | | |
|---|---|---|---|
| 5,451,789 A | 9/1995 | Wong et al. | |
| 5,453,623 A | 9/1995 | Wong et al. | |
| 5,502,303 A | 3/1996 | Gonzalez-Lepera | |
| 5,543,622 A | 8/1996 | Stearns | |
| 5,687,208 A | 11/1997 | Bae et al. | |
| 5,961,457 A | 10/1999 | Raylman et al. | |
| 6,083,008 A * | 7/2000 | Yamada et al. | 434/267 |
| 6,266,649 B1 | 7/2001 | Linden et al. | |
| 6,462,342 B1 | 10/2002 | Stearns | |
| 6,490,475 B1 | 12/2002 | Seeley et al. | |
| 6,793,496 B2 | 9/2004 | Edic et al. | |
| 2001/0051913 A1 | 12/2001 | Vashistha et al. | |
| 2002/0023735 A1 | 2/2002 | Uchikawa et al. | |
| 2002/0046074 A1 | 4/2002 | Barton | |
| 2002/0123983 A1 | 9/2002 | Riley et al. | |
| 2004/0225549 A1 | 11/2004 | Parker et al. | |
| 2004/0225554 A1 | 11/2004 | Chiappetta et al. | |

OTHER PUBLICATIONS

Kimura et al. Phys. Med. Biol. 47 (2002) 455-468.*
Kimura et al. "Fast formation of statistically reliable FDG parametric images based on clustering and principal components" Phys. Med. Biol. 47 (2002), pp. 455-468.*
H. Zaidi, "Relevance of Accurate Monte Carlo Modeling in Nuclear Medical Imaging" Med. Phys. 26 (4), 574-608, 1999.

(Continued)

*Primary Examiner* — Brian Casler
*Assistant Examiner* — Nasir Shahrestani
(74) *Attorney, Agent, or Firm* — Scott J. Asmus

(57) ABSTRACT

A nuclear medicine imaging simulator system is provided for simulating nuclear imaging of a target within a phantom using a selected pharmacokinetic model. The system includes a processor assembly having at least one processor receiving a digital phantom model and a digital pharmacokinetic model, and a dynamic integration module executable on the processor assembly for integrating the pharmacokinetic model with the phantom model to generate a dynamic phantom data representing activity of the pharmacokinetic model within the phantom model over simulated time. The system further includes an imager module executable on the processor assembly for generating a digital imager model representing a nuclear imager in accordance with at least one selectable imager parameter that controls activity of the imager model relative to simulated time, and an imager simulator module executable on the processor assembly for processing the dynamic phantom data with the imager model for simulating at least one imaging process of the dynamic phantom data in accordance with the at least one imager parameter and generating respective simulated sensed data in accordance with individual imaging processes of the at least one imaging process.

28 Claims, 6 Drawing Sheets

OTHER PUBLICATIONS

I. G. Zubal, C. R. Harrell, and P. D. Esser, "Monte Carlo Determination of Emerging Energy Spectra for Diagnostically Realistic Radiopharmaceutical Distributions." Nucl. Instrum. Methods Phys. Res. A 299, 544-547, 1990.

J. C. Yanch, A. B. Dobizeniecki, C. Ramanathan, and R. Behrman, "Physically Rrealistic Monte Carlo Simulation of Source Collimator and Tomographic Data Acquisition for Emission Computed Tomography," Phys. Med. Biol. 37, 853-870, 1992.

C. J. Thompson, J.-M. Cantu, and Y. Picard, "PETSIM: Monte Carlo program simulation of all sensitivity and resolution parameters of cylindrical positron imaging systems," Phys. Med. Biol. 37, 731-749, 1992.

R. L. Harrison, S. D. Vannoy, D. R. Haynor, S. B. Gillispie, M. S. Kaplan, and T. K Lewellen, "Preliminary experience with the photon history generator module for a public-domain simulation system for emission tomography," in Conf. Rec. IEEE Med. Imag. Conf., San Francisco, pp. 1154-1158, 1994.

L. Sokobff, M. Reivich, C. Kennedy, M.H. Des Rosiers, C.S. Patlak, K.D. Pettitgrew, O. Sakurda and M. Shinohara, "The [11-C]Deoxyglucose, method for rhw measurement of local cerebral glucose utilization: Theory, procedure and normal values in conscious and anesthetized albany rat", J. of Neurochem. vol. 28, 897-916, 1977.

M. Reivich, A. Alavi, A. Wolf, J Fowler, J. Russel, C. Arnett, R.R. MacGregor, C.Y.Shlue, H. Atkins, A. Anand, R. Dann and J.H. Greenberg, "Glucose Metabolic Rate Kinetic Model Parameter Determination in Humans: The Lumped Constants for [18-F]Fluorodeoxyglucose and [11-C]Deoxyglucose", J. of Cerebral. Blood Flow and Meta., 5, 179-192, 1985.

R. Jain, "Transport of molecules in the tumor interstitium: A review," Cancer Research. 47, 3039-3051, 1987.

L.T. Baxter, H. Zhu, D.G. Mackensen, W.F. Butler and R.K. Jain, "Biodistribution of monoclonal antibodies: scale-up from mouse to humans using a physiologically based pharmacokinetic model," Cancer Research. 55, 4811-4522, 1995.

M. Praxmarer, C. Sung, P.M. Bungay, and W.W. van Osdol, "Computational Models of Antibody-Based Tumor Imaging", Annals of Biomedical Engineering, vol. 29, pp. 340-358, 2001.

Sung, C., and W. W. van Osdol. "Pharmacokinetic comparison of direct antibody targeting with pretargeting protocols based on streptavidin-biotin binding" J. Nucl. Med. 36:867-876, 1995.

Your Ref. No. RD124114/10761 Application No. GB 0511876.1; Patents Act 1977; Examination Report under Section 18(3); 4 Pages.

* cited by examiner

SIMULATION OF NUCLEAR MEDICAL IMAGING

FIELD OF THE INVENTION

The present disclosure relates to nuclear medical imaging simulation, and particularly to the use of a dynamic pharmacokinetic model in simulation of nuclear medical imaging.

BACKGROUND OF THE INVENTION

Radionuclides are employed as radioactive labels, or tracers, by incorporating them into molecules to produce a radiolabeled probe. The probes are introduced into a patient (source) and become involved in biological processes, such as blood flow, fatty acid, glucose metabolism, and protein synthesis. The probes can also be formulated to accumulate differently in targeted tissue (a target), such as an organ of interest, relative to other tissue, such as due to elevated (or diminished) rates of glucose metabolism in diseased cells compared to normal tissue. Alternatively, targeting can be achieved by using probes having engineered antibodies or anti-body fragments that bind to receptors present in target tissue, such as, for example the -Her2-Neu receptor overexpressed by breast cancer cells. A widely used -imaging probe, 18-Fluoro-deoxyl-glucose (FDG), has been used, for example, in vivo for imaging of cancer, neuro-degenerative disease and cardiovascular disease. Similarly, Alzheimer's disease can be detected by using probes that target beta amyloid, which tends to accumulate in a diseased brain.

As the radionuclides decay, they may emit either gamma rays or positrons. In the case of positron emission, the positrons travel a very short distance before they encounter an electron, and when this occurs, they are annihilated and converted into two photons, or gamma rays. By measuring the number of pairs of photons emitted in the target relative to the other tissue, organ characteristics or irregularities can be studied. In the case of direct gamma ray emission, by measuring the number of gamma rays emitted in the target relative to the other tissue, organ characteristics or irregularities can be studied Currently, nuclear medical imaging includes Planar Gamma Camera Imaging, Single-Photon Emission Computed Tomography (SPECT), Positron Emission Tomography (PET) and Multiple Emission Tomography (MET). Planar Gamma Camera Imaging is performed by a gamma camera, such as an Anger camera, having a collimator typically made of lead or tungsten having a plurality of channels, and a scintillation crystal placed under the collimator. Gamma rays traveling along a path that coincides with a path defined by any of the channels pass through the channel unabsorbed and interact with the crystal for producing a light signal. An array of light sensors, such as photomultiplier tubes (PMTs), is provided behind the crystal to detect the light and generate an intensity signal indicative of the amount of light detected at each sensor. A planar image is constructed in accordance with the intensity signal and the direction from which the associated gamma signal came from. SPECT includes generation of a 3-dimensional image by generating and reconstructing a plurality of planar images from different angles using a tomographic process.

In a PET scanner, characteristics of two aspects of the annihilation of positrons are of particular interest; each gamma ray has an energy of 511 keV, and the two gamma rays are directed in nearly opposite directions. The PET scanner is typically cylindrical, and includes a collimator for rejecting scatter events, and a detector ring assembly composed of rings of detectors which encircle the patient, and which convert the energy of each 511 keV photon into a flash of light that is sensed, such as by a PMT. Coincidence detection circuits connect to the detectors and record only those photons which are detected simultaneously by two detectors located on opposite sides of the patient. The number of such simultaneous events (coincidence events) indicates the number of positron annihilations that occurred along a line joining the two opposing detectors. Within a few minutes hundreds of millions of coincidence events may be recorded indicative of the number of annihilations along lines joining pairs of detectors in the detector ring. These numbers are employed to reconstruct an image using well-known computed tomography techniques. MET utilizes two-different crystals positioned in a sandwich-like construction for allowing simultaneous use of gamma emitting and positron emitting radiolabeled probes.

There are many factors during the imaging process, which affect the degree of qualitative and quantitative accuracy of the image produced. Such factors include, for example, selection, configuration, placement and/or function of components of the nuclear scanner, including collimator dimensions, source-to-detector distance, resolution of the gamma camera; timing and duration of image capture; image reconstruction techniques; and composition of the source. However, due to expense of the radionuclides and imaging probe, the ill-effects of exposure of the patient to the radionuclides, expense of test administration, and difficulty in separating out single factors of the entire imaging process in an experimental situation, it is generally impractical to empirically study or make adjustments to the imaging process. Evaluation of probes has commonly been performed through animal experiments and subsequent human trials; however the process is inefficient, slow and expensive.

Accordingly, tools have been developed, such as described by J. C. Yanch et al. in "Physically Realistic Monte Carlo Simulation of Source, Collimator and Tomographic Data Acquisition For Emission Computed Tomography", Phys. Med. Biol., Volume 37, No. 4, 1992, pp 853-870, for simulation of nuclear imaging, in which a user may input information detailing configuration of the nuclear imaging scanner including the number of tomographic views; the source, including geometries within, and "the 3D distribution of the isotope and various attenuating materials . . . distributed in any spatial configuration throughout an organ inside the human body or head"; and image reconstruction parameters, including energy windows and energy sampling functions.

However, the image generated by simulated nuclear imaging is limited to providing spatial information at a specific point in time corresponding to the input time of the data associated with the simulated isotope distribution. However, due to the nature of isotopes, the real isotope distribution varies over time.

Accordingly, there is a need for a system and method for simulated nuclear medicine imaging which accounts for temporal changes in isotope distribution.

BRIEF DESCRIPTION OF THE INVENTION

A nuclear medicine imaging simulator system is provided including a processor assembly having at least one processor receiving a digital phantom model and a digital pharmacokinetic model, and a dynamic integration module executable on the processor assembly for integrating the pharmacokinetic model with the phantom model to generate dynamic phantom data representing activity of the pharmacokinetic model within the phantom model over simulated time. The system further includes an imager module executable on the processor assembly for generating a digital imager model representing a nuclear imager in accordance with at least one selectable imager parameter that controls activity of the imager model relative to simulated time, and an imager simulator module executable on the processor assembly for processing the dynamic phantom data with the imager model for simulating at least one imaging process of the dynamic phantom data in accordance with the at least one imager parameter and generating respective simulated sensed data in accordance with individual imaging processes of the at least one imaging process.

In another embodiment a method is provided for simulating a nuclear imaging process including the steps of providing for receiving of a digital phantom model and a digital pharmacokinetic model, providing for integration of the pharmacokinetic model with the phantom model to generate dynamic phantom data representing activity of the pharmacokinetic model within the phantom model over simulated time. The method further includes the steps of providing for generation of a digital imager model representing a nuclear imager in accordance with at least one selectable imager parameter, wherein the at least one imager parameter controls activity of the imager model relative to simulated time; providing for processing of the dynamic phantom data with the imager model for simulating at least one imaging process of the dynamic phantom data in accordance with the at least one imager parameter; and providing for generation of respective simulated sensed data in accordance with individual imaging processes of the at least one imaging process.

Steps of the method of the invention may be implemented by executing instructions on a processor, where the instructions are stored on a computer readable medium or included in a computer data signal embodied in a transmission medium.

DESCRIPTION OF THE PREFERRED EMBODIMENT

Figure 1:
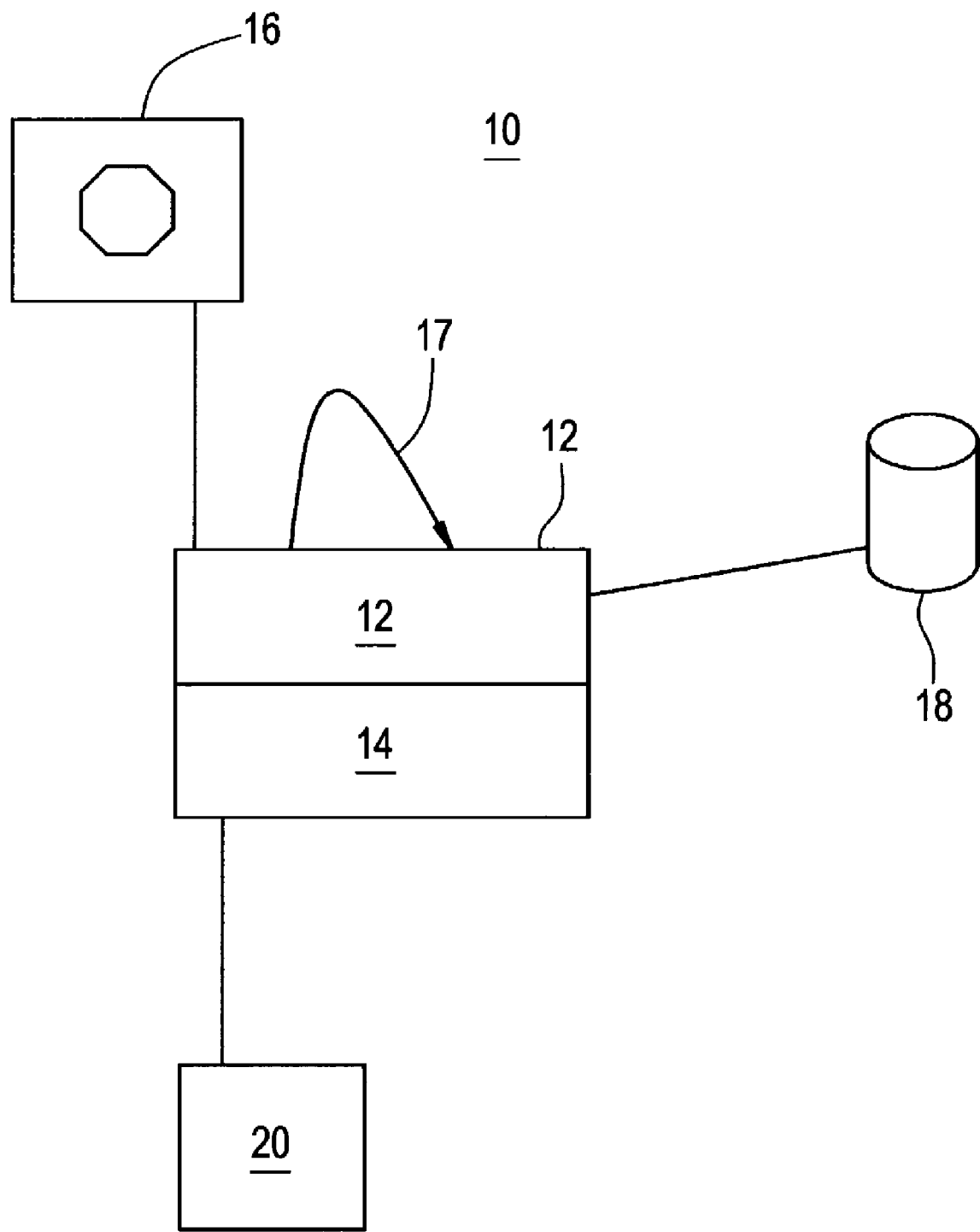
FIG. 1 is a block diagram of an illustrative embodiment of a nuclear medicine imaging simulation system.

Referring to FIG. 1, a nuclear medicine imaging simulation system 10 is shown, including a processor assembly 11 including at least one processor 12 and/or circuitry 14. The processor assembly 11 generates a phantom model, a pharmacokinetic model and a nuclear imager model in accordance with a set of respective phantom, pharmacokinetic and imager parameters, processes the models for simulating an imaging process of the phantom model in accordance with the nuclear imager model including dynamic processes corresponding to the pharmacokinetic model, and generates simulated sensed data in accordance with the simulated imaging. The processor assembly 11 further processes the simulated sensed data to generate an image corresponding to image data of the simulated sensed data. The image data may be provided to a display device 16 for display thereof. The processor assembly 11 further analyzes the image data and the corresponding image. The results of the analysis are processed for determining adjusted imaging parameters to provide as feedback data 17 for reconfiguring the pharmacokinetic model and/or the imager model.

The processor 12 accesses storage 18 for accessing stored data and software instructions for performing the above processes. At least one user input device 20 is provided for allowing a user to input data such as imaging parameter data to the processor 12, and for entering user requests, such as for requesting initiation of a process by the processor 12 and or circuitry 14.

The processor 12 may include one or more processors, including parallel processors, networked processors, PDA's, handheld devices having microprocessors or other computing devices. The storage 18 may include one or more storage devices, such as a hard drive, a removable storage device, such as a CD-ROM, a remote storage device, etc. The circuitry 14 may include firmware, one or more integrated circuits, logic circuitry, circuitry for processing analog signals, etc.

Figure 2:
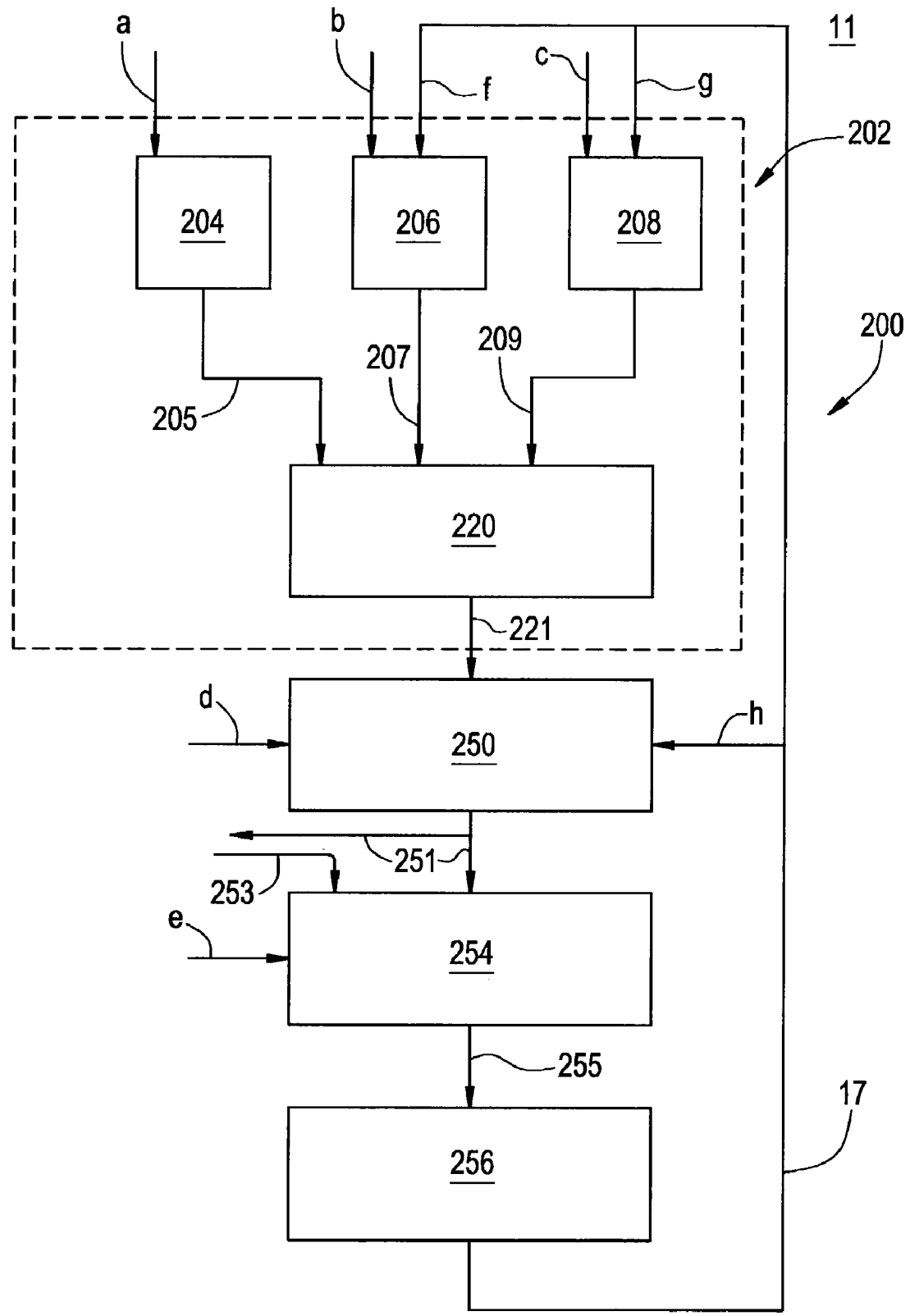
FIG. 2 is a functional block diagram of processing components of the system shown in FIG. 1

Referring to FIG. 2, a functional block diagram of a set of processing components 200 of the processor assembly 11 is shown. The set of processing components 200 includes a subset of processing components 202, having a phantom module 204 that generates a digital phantom model 205, a pharmacokinetic module 206 that generates a digital pharmacokinetic model 207, a nuclear imager module 208 that generates a digital nuclear imager model 209 and a simulator module 220 receiving the models 205, 207 and 209 and generating simulated sensed data 221. The modules 204, 206, 208 and 220 are preferably software modules including software instructions executable by the processor 12. The modules 204, 206, 208 and 220 may further include signals or instructions processed by circuitry 14. The phantom module 204, pharmacokinetic module 206 and nuclear imager module 208 may include algorithms that are commercially available for generating the respective models 205, 207 and 209.

The models 205, 207 and 209 are each generated in accordance with imaging parameter data that may be input, calculated and/or retrieved from storage. Preferably a user interface is provided for allowing a user to enter imaging parameters to each of modules 204, 206 and 208 for generating the desired respective models 205, 207 and 209.

With respect to the phantom module 204, a library of digital phantom models may be stored in storage 18, where the user may select one of the phantom models, a portion of a phantom model and/or alter or add to the selected phantom model in accordance with entered phantom parameters "a". For example, a library of phantom models may be stored including a phantom model that are representative of the anatomy of typical males and females of varying ages of average size and weight. Anatomic compartments of the model may include, for example, blood vessels for transporting the imaging probe, organs, and characteristics of normal tissue. The user may enter or select phantom parameters "a", including gender and age, to select a phantom model 205. The user may further enter or select phantom parameters "a" such as weight and size of the represented person and region or organ of interest. Furthermore, the user may enter or select phantom parameters "a" representative of an abnormality, such as a lesion of a selected size at a selected location within the phantom model 205.

With respect to the pharmacokinetic module 206, a library of various radionuclide and probe models are stored in storage 18, where the user may select at least one combination of a selected radionuclide model and a selected probe model for forming a pharmacokinetic model 207, and/or alter or add to the selected radionuclide and probe model(s) in accordance with entered or selected pharmacokinetic parameters "b". For example, a library of radionuclide models and a library of probe models may be stored that are representative of known radionuclides and known probes, respectively. Pharmacokinetic parameters "b" associated with the radionuclide model and the probe model affect the expected behavior of the formed pharmacokinetic model 207 over time when processed with the phantom model 205. The pharmacokinetic parameters "b" include half-life of the radionuclide model, gamma yield of radionuclide model, factors which influence the rate at which the pharmacokinetic model 207 is processed by tissues modeled in the phantom model 205, mono-clonal antibodies included in the probe model, diffusion rate of the pharmacokinetic model 207, clearance rate of the probe model from background tissue included in the phantom model 205, where the background tissue is tissue not targeted by the pharmacokinetic model 207, binding affinities for a specific target included in the phantom model 205, dosage of the radioisotope modeled in the radioisotope model and dosage of the probe modeled in the probe model.

In one embodiment, the physics associated with an imaging modality or scanner is modeled by the imager module 208. With respect to the imager module 208, a library of one or more digital imager modules is stored in storage 18, where the user may select the desired imager model 209, and configure the imager model 209 in accordance with entered or selected imager parameters "c", including detector and system geometry configurations, timing and energy windows, sensitivity and resolution of the imager model 209. For an imager model 209 representative of a PET scanner, the system geometry configuration parameter may, for example, represent the length and diameter of the bore into which the patient is inserted. For an imager model 209 representative of a SPECT scanner, the geometry configuration imaging parameter may, for example, represent the shape and dimensions of the collimator. The resolution and sensitivity parameters may be representative of the collimator configuration as well as the configuration of the crystal, the sensor array and other circuitry for processing of the sensed signals of the imager being modeled, the field of view, the number of angular views used, etc.

In addition, selectable imager parameters "c" of the imager model 209 may include timing parameters, including acquisition wait time and acquisition duration (scan) time. The selectable imager parameters "c" of the imager model 209 may further include imaging parameters for affecting processing of the simulated signals, including filtering, amplification, sampling, weighting thereof, threshold values, such as for voltage windows, time coincidence windows, angle windows, energy windows etc. Other selectable imaging parameters include reconstruction parameters "d" for performing image reconstruction of the simulated sensed signals, including selection of algorithms used and selection of selectable constants used in the selected algorithm.

Figure 3:
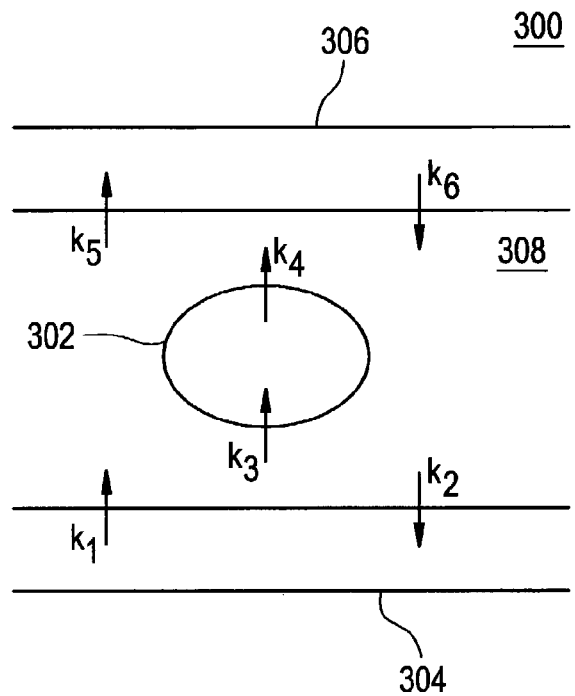
FIG. 3 is a diagrammatical representation of a flow of radio labeled imaging probe.
Figure 4:
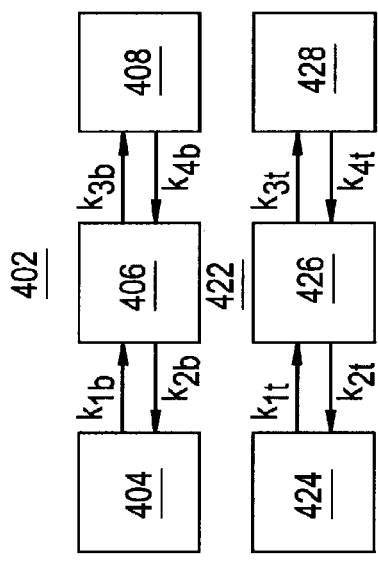
FIG. 4 is a diagrammatical representation of pharmacokinetic flow.
Figure 5:
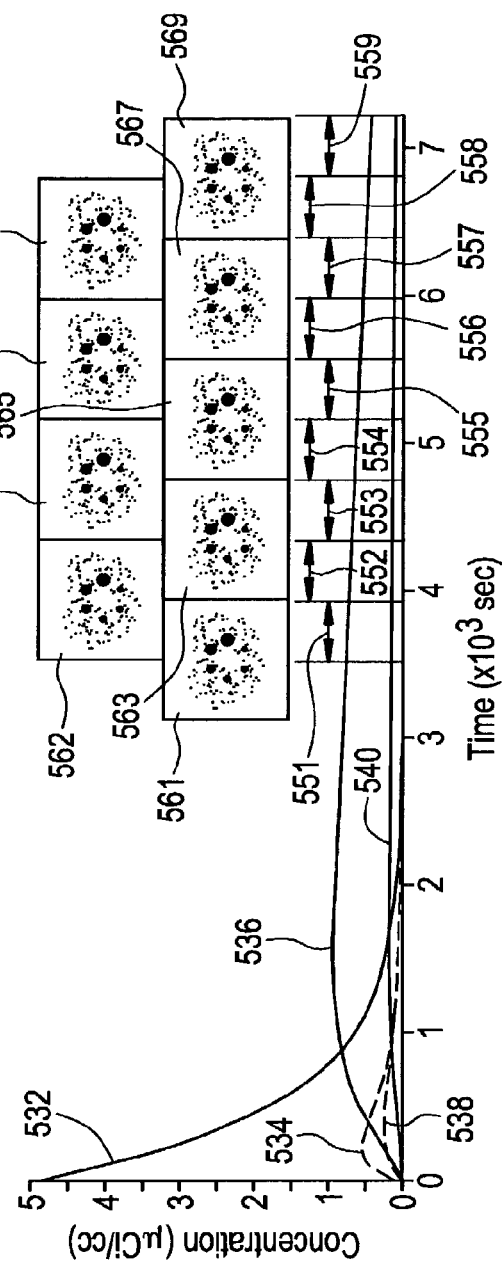
FIG. 5 is a plot in accordance with equations representing concentration levels of a radionuclide over time.

The simulator module 220 receives the models 205, 207 and 209 and simulates introduction of the pharmacokinetic model 207 into the phantom 205 and the activity of the introduced radio-labeled imaging probes over time, as diagrammed in FIGS. 3-5, where FIG. 3 shows a diagrammatic representation of a pharmacokinetic model 300, including the flow of a selected radio-labeled imaging probe through the circulatory system, and into and out of a target 302, including to and from a blood vessel, such as a capillary 304, to and from lymphatics 306 and to a from normal tissue 308 which is a tumor, at a selected point in time, where $k_1$-$k_6$ represent diffusion coefficients that correspond to the selected probe model.

FIG. 4 is a diagrammatic representation of pharmacokinetic flow of a selected radio-labeled image probe between blood plasma and background tissue, as shown in flow diagram 402, and blood plasma and tumor tissue, as shown in flow diagram 402. In flow diagram 402, element 404 represents "$C_p$", the concentration of the radionuclide (i.e., 18-Fluoro-deoxylglucose (FDG)) of the radio-labeled probe in plasma, element 406 represents "$C_{eb}$" the concentration of the radionuclide (i.e., FDG) in background tissue during an initial stage of metabolism, and element 408 represents "$C_{mb}$", the concentration of the radio nuclide (i.e., FDG-6P) in the background tissue during a strapping (binding) stage of metabolism. In flow diagram 422, element 424 represents "$C_p$", the concentration of the radionuclide (i.e., FDG) in plasma, element 426 represents "$C_{et}$" the concentration of the radionuclide (i.e., FDG) in tumor tissue during the initial stage of metabolism, and element 428 represents "$C_{mt}$", the concentration of the radio nuclide (i.e., FDG-6P) in the tumor tissue during the strapping stage of metabolism.

Equations (1), (2) and (3) below represent, respectively, simulation concentration of a radionuclide in plasma over time, rate of change over time of concentration of the radionuclide at the initial stage of metabolism, and rate of change over time of concentration of the radionuclide at the strapping stage of metabolism, where subscript "$_i$" may substituted with "$_b$" for background or "$_t$" for tumor.

$$C_p = 5 * e^{-at} \quad (1)$$

$$\frac{dC_{ei}}{dt} = k_{1i}C_p - (k_{2i} + k_{3i} + \lambda)C_{ei} + k_{4i}C_{mi} \quad (2)$$

$$\frac{dC_{mi}}{dt} = k_{3i}C_{ei} - (k_{4i} + \lambda)C_{mi} \quad (3)$$

FIG. 5 shows plots for equations (1), (2) and (3) in an exemplary simulation of an introduced selected radio-labeled image probe, where plot 532 is $C_p$, plot 534 is $C_{et}$, plot 536 is $C_{mt}$, plot 538 is $C_{eb}$ and plot 540 is $C_{mb}$. Accordingly, the plots 532, 534, 536, 538, 540 represent incorporation of the dynamic time sensitive pharmacokinetic model 207 into the phantom model 205, resulting in a dynamic combined phantom/pharmacokinetic model that changes over time.

With reference again to FIG. 2, the simulator module 220 processes the dynamic phantom/pharmacokinetic model 207 with the imager model 209, where the imager model 209 is configured to begin a scan process at a selected time (acquisition wait time) for a selected duration of time (acquisition duration time), in accordance with the selected time-sensitive imager parameters. The imager model 209 may be configured to perform successive scans. The duration of real time scans is generally in the order of minutes, and a scan is typically initiated when a previous scan has completed. With reference to FIG. 5, in the exemplary simulation, a series of scans were processed. A first scan 551 a was initiated at time=3600 sec, for a duration of 300 sec, followed by a series of consecutive, back-to-back scans 552-559, each having a duration of 300 sec.

As the simulator processes the imager model 209 and the radio labeled imaging probe concentrations in the various anatomic compartments from the dynamic phantom/pharmacokinetic model and generates simulated sensed data 221 representative of the signals generated by sensors in an actual nuclear imager. The imager model 209 may employ an analytical model or a more extensive Monte-Carlo model of an imaging system, both of which are capable of accounting for processes such as the attenuation of energy through surrounding tissue, the geometric and intrinsic sensitivity and point-spread function of the sensors, filtering circuitry, amplification circuitry, buffering circuitry, analog to digital conversion circuitry, etc. The simulated sensed data 221 provide data indicative of concentrations of the selected radio-labeled image probe(s) within a region lying within the field of view of the imager model 209, providing concentration of the selected radio-labeled imaging probes information at a selected point in time for providing spatially-sensitive and time-sensitive information. Accordingly, the processing performed by the subset of processing components 202 is a function of space and time.

Figure 6:
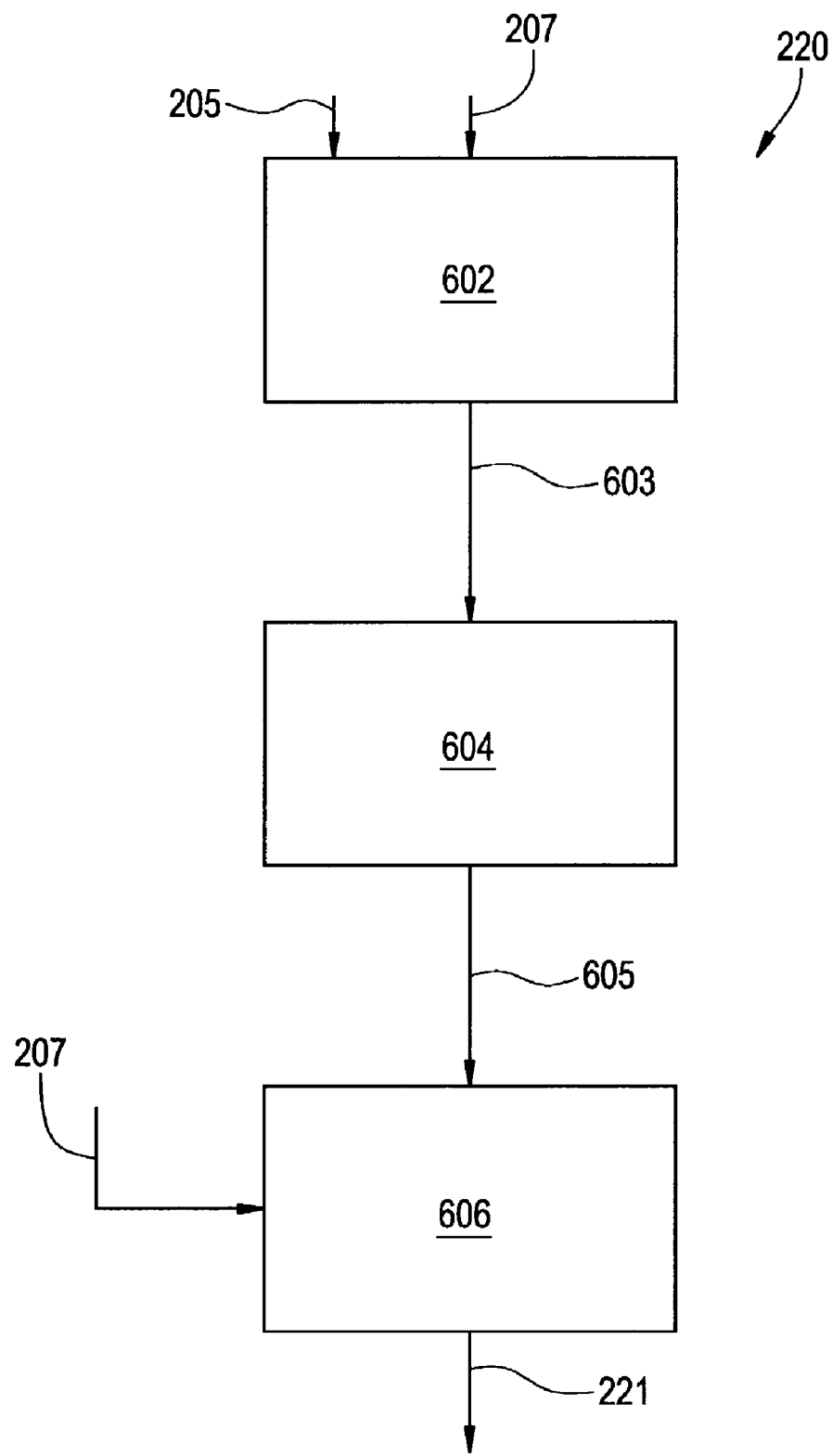
FIG. 6 is a block diagram of a simulator module of the system shown in FIG. 1.

FIG. 6 shows a block diagram of components of the simulator module 220, including a curve generator module 602, a conversion module 604 and an imager simulator module 606, where the curve generator module 602 and the conversion module 604 form a dynamic integration module 608. The curve generator module 602 receives the phantom model 205 and the pharmacokinetic model 207 and generates time activity curves (TACs) 603, which are continuous curves representative of the concentration levels over time of the radio-labeled imaging probe within the various compartments of the phantom model 207. The TACs 603 are processed by the conversion module 604 for generating discrete values 605 including the discrete number of positron or gamma ray emissions within discrete time intervals. The imager simulator module 606 receives the imager model 209, including the time sensitive parameters including acquisition wait time and acquisition duration time for each scan to be performed, and processes the discrete values 605 with the imager model 209 to generate image data 221 representing simulated image data output for each scan.

In one embodiment, the set of processing components 200 shown in FIG. 2 further includes an image reconstruction module 250, an image analysis module 254 and an adjustment control module 256, all of which are software modules including programmable instructions executable on the processor 12. The modules 250, 254 and 256 may further include signals or instructions processed by circuitry 14. The image reconstruction module 250 receives and processes the simulated sensed data 221 in accordance with an image reconstruction algorithm, as is known in the art, and generates image data 251 indicative of the simulated sensed data 221. The image data 251 may be provided to the display device 16 of FIG. 1 for display thereof as an image 253. FIG. 5 shows a series of images 561-569, which were generated from the image scans 351-359. The image data 251 and/or image 253 may further be provided to the image analysis module 254 for analysis thereof. A user may enter or select reconstruction parameters ""d" to the image reconstruction module 250, where the reconstruction parameters "d" control selection of the algorithm to be used and/or parameters of the algorithm, such as resolution, sampling rate, filtering algorithms and related coefficients or thresholds, etc.

The image analysis module 254 receives the image data 251 and/or the image 253, and analyzes the received data for computing an image quality metric 255. As is apparent from FIG. 5, the images 561-569 vary in image quality, and an analysis of the image quality can be used to determine optimum imaging parameter choice, which in this example is acquisition wait time.

The image quality metric 255 includes a quantitative metric, such as a contrast-to-noise ratio, a source to background ratio, noise-equivalent count rates etc., and/or a lesion detectability metric. The lesion detectability metric is typically a result of a subjective analysis. The lesion detectability metric may be computed using computational observer models, such as the channelized Hotelling observer (CHO) model, which mimics lesion detection by typically average human observers, as known in the art. In addition to, or instead of the metric computed by the image analysis module 252, the lesion detectability metric may include results of actual lesion detection experiments in which the images 253 are presented to one or more human observers that generate a lesion detectability score. The image quality metric analysis is performed in accordance with the needs of the task being performed. Depending on the application, the image quality may be analyzed for a variety of qualities or quantities.

The image quality metric 255 is provided to the adjustment control module 256 for processing thereof, such as for outputting feedback data 17 including adjusted imaging parameters including pharmacokinetic parameters provided as pharmacokinetic parameters "f" to the pharmacokinetic module 206, as imager parameters "g" to the imager module 208, and/or as reconstruction parameters "h" to the image reconstruction module 254.

A series of simulated imaging process may be repeated, each using the adjusted imaging parameters from the previous simulated imaging process. In one embodiment, the adjustment control module 256 compares the image quality metric 255 generated for each of the simulated imaging processes performed, and outputs data corresponding to the simulated imaging process having the optimal image quality metric 255, where the output data preferably includes the imaging parameters used for obtaining the optimal image quality metric 255. Accordingly, the imaging parameters output with the output data are the optimal imaging parameters for the application being studied.

Figure 7:
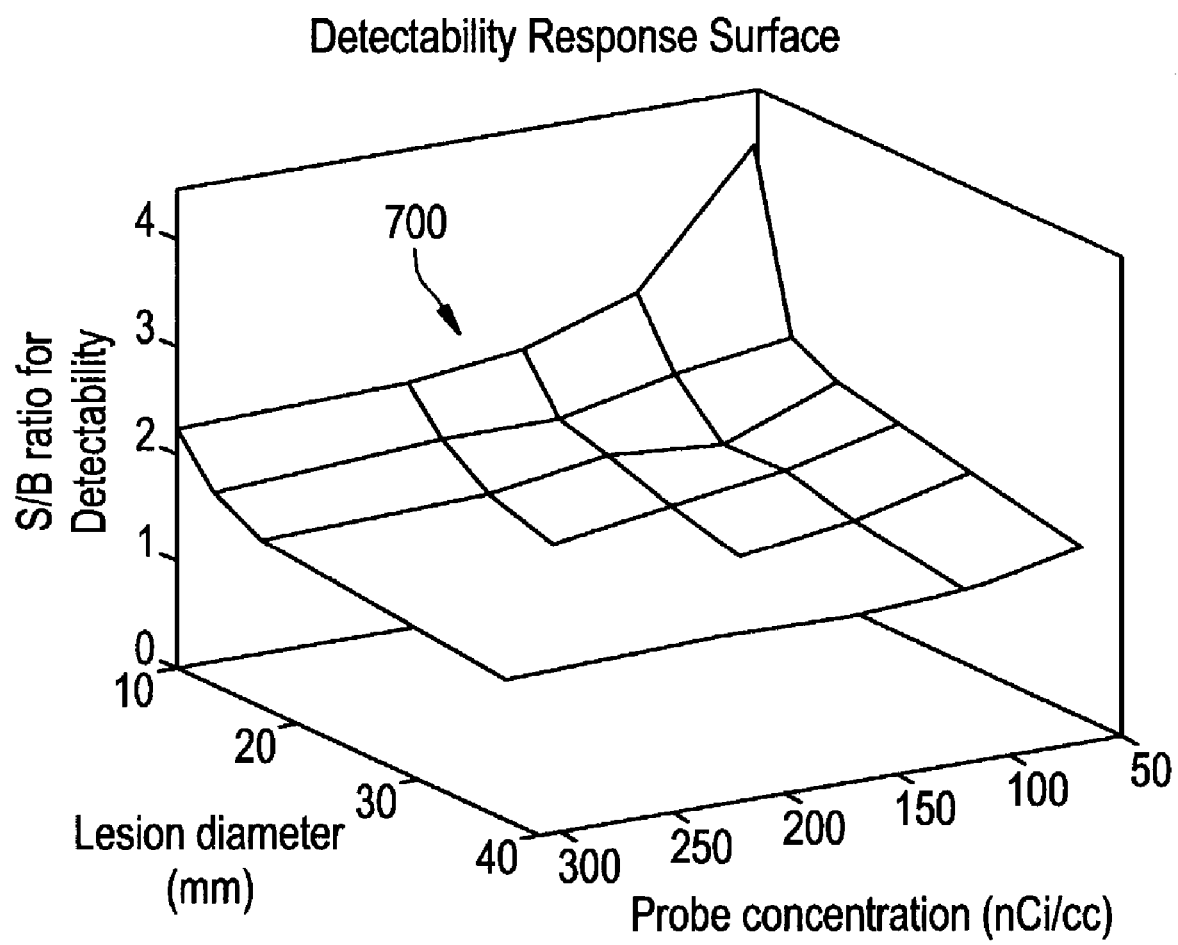
FIG. 7 is a plot of a detectability response surface for determining lesion detectability as a function of background imaging probe concentration.

A computational and/or graphical hyper-surface and/or function optimization algorithm may be generated/computed as a function of selected imaging parameters for optimizing the selected imaging parameters for achieving a desired operating point for the application being performed. An exemplary hyper-surface 700 (a detectability response surface) is shown in FIG. 7, in which probe concentration in the background tissues is varied for imaging of lesions of various diameters. The hyper-surface 700 was generated from an experiment in which simulated images generated for lesions of a variety of sizes using a variety of probe concentrations were displayed to five observers who determined lesion detectability. The hyper-surface 700 indicates the level of source-to-background (SIB) ratio required for detectability of a lesion of given size. The higher source-to-background contrast ratio indicates that a larger concentration of the probe is required within the lesion having the corresponding lesion diameter.

Using a simulation model such as the Monte-Carlo model, a degree of randomness is introduced into each imaging process, so that repeated simulated imaging processes having the same imaging parameter settings are not necessarily identical, similar to the introduction and imaging of in vitro radiolabeled imaging probes. Accordingly, optimal imaging parameters may further be tested for accurate and repeatable results within specifications needed for the task being performed. Further adjusting of the imaging parameters may be performed until sufficient accuracy and repeatability is obtained for the current specifications.

The optimal imaging parameters are used, for example, by medical professionals for obtaining optimal images of a patient, and may further be used for specifications for the production of probes, radioisotopes and imagers not yet available.

The imaging simulation system 10 may further be used for automatically repeating an image process while generating different imaging parameters including phantom parameters "a" to the phantom module 204 for performing a series of imaging processes to find optimal phantom parameters for each of the different phantom model 205 configurations, such as for lesions of different sizes or located in different types of normal tissue.

Figure 8:
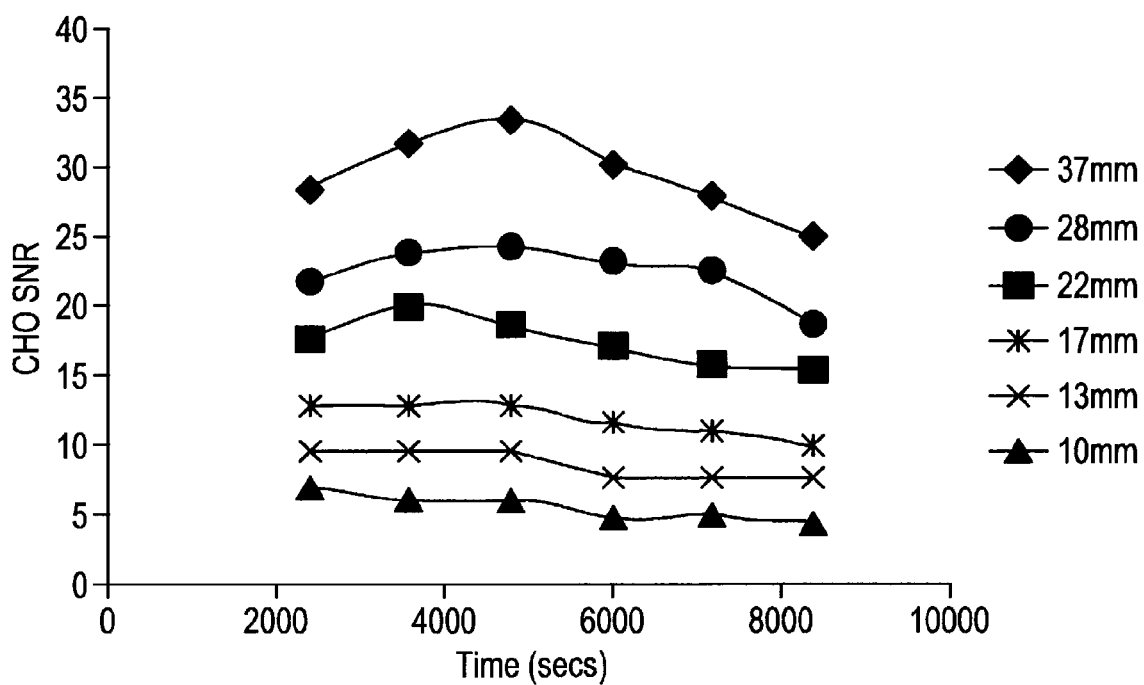
FIG. 8 is a plot of experimental results for tumor detectability as a function of tumor size and acquisition wait time.

An example of a study of imaging of lesions of different sizes is shown in FIG. 8, in which a plot is shown of experimental results obtained using a model of a GE Discovery™ LS PET/CT scanner developed by General Electric Corporation to generate images of a NEMA™ 2001 phantom with tumors ranging in diameter from 10 mm-37 mm. A variation of the Sokoloff model for FDG was used to generate time activity curves (TACs) for untreated lung cancer tumors using published kinetic parameters. The TACs were converted to discrete values and input to the scanner to obtain dynamic images of the phantom. Tumor and background activities varied as predicted by the model TACs. Six sets of 300 s acquisition dynamic images were generated for acquisition wait times from 2400 s-8400 s after injection. Tumor detectability was estimated with a CHO model having nine spatial frequency channels.

The results depicted in FIG. 8 show that although tumor contrast increased over time of all tumors, tumor detectability for tumors up to 17 mm in diameter decreased monotonically with acquisition start times, while for tumors 22 mm and larger, detectability increased up to 4200 s before decreasing monotonically. The optimal start times increased with increasing tumor size. Accordingly, the experiment performed shows detectability as a function of tumor size and acquisition wait time. The results indicate that despite improved tumor contrast for late acquisitions, detectability of small tumors decreased due to the increased noise, while large tumors were more tolerant to image noise.

Exemplary applications for use with the present disclosure include evaluation and screening of specific imaging probes and radionuclides for imaging cancer, neuro-degenerative disease, cardio-vascular disease, etc.; evaluation of strategies for targeting the disease, including direct targeting with a probe or pre-targeting; optimization of image acquisition parameters including dose of administered radio-isotope, wait time before image acquisition based on the biological and radio-isotope half-life, duration of the image acquisition time, etc.

The described embodiments of the present disclosure are intended to be illustrative rather than restrictive, and are not intended to represent every embodiment of the present disclosure. Various modifications and variations can be made without departing from the spirit or scope of the present disclosure as set forth in the following claims both literally and in equivalents recognized in law.

What is claimed is:

1. A nuclear medicine imaging simulator system comprising:

a processor assembly including at least one processor receiving a digital phantom model and a digital pharmacokinetic model;

a dynamic integration module executable on the processor assembly for integrating the pharmacokinetic model with the phantom model to generate dynamic phantom data representing activity of the pharmacokinetic model within the phantom model over simulated time;

an imager module executable on the processor assembly for generating a digital imager model representing a nuclear imager in accordance with at least one selectable imager parameter that controls activity of the imager model relative to simulated time;

an imager simulator module executable on the processor assembly for processing the dynamic phantom data with the imager model for simulating at least one imaging process of the dynamic phantom data in accordance with the at least one imager parameter and generating respective simulated sensed data in accordance with individual imaging processes of the at least one imaging process;

an image analysis module executable on the processor assembly for receiving image data associated with the respective simulated sensed data and generating an image quality metric indicative of quality of the associated image data based on an analysis selected from the group consisting of a qualitative analysis and a quantitative analysis; and an adjustment control module executable on the processor assembly for generating at least one adjusted parameter for selecting at least one imager parameter, at least one pharmacokinetic model, at least one phantom model, or combinations thereof, for use with at least one future imaging process in accordance with the image quality metric.

2. The simulator system in accordance with claim 1, wherein the at least one imager parameter is selected from the group consisting of acquisition wait time and acquisition duration time associated with individual imaging processes.

3. The simulator system in accordance with claim 2, wherein individual imaging processes of the at least one imaging process begin at the associated selected acquisition wait time and continue for the duration of the associated selected acquisition duration time.

4. The simulator system according to claim 1, further comprising an image reconstruction module executable on the processor assembly for receiving the respective simulated sensed data and generating associated image data in accordance with the respective simulated sensed data.

5. The simulator system according to claim 4, wherein the image reconstruction module provides the image data associated with the respective simulated sensed data to a display device for generating an associated image thereof.

6. The simulator system according to claim 1, further comprising a pharmacokinetic module for generating the pharmacokinetic model in accordance with at least one selectable pharmacokinetic parameter that controls the activity of the pharmacokinetic model within the phantom model over simulated time, wherein the at least one adjusted parameter is generated for selecting a parameter selected from the group consisting of the at least one imager parameter and the at least one pharmacokinetic parameter for use with a future imaging process in accordance with the image quality metric.

7. The simulator system according to claim 1, wherein the adjustment control module compares the image quality metric generated for an image or image data associated with simulated sensed data associated with respective at least first and second imaging processes, wherein the at least first and second imaging processes use different parameters selected from the group consisting of the at least one imager parameter and the at least one pharmacokinetic parameter.

8. The simulator system according to claim 7, wherein the adjustment control module determines the parameters used for the imaging process of the at least first and second imaging processes having an optimal image quality metric.

9. The simulator system according to claim 1, further comprising a phantom module for generating the phantom model in accordance with at least one selectable phantom parameter.

10. The simulator system according to claim 1, further comprising a pharmacokinetic module for generating the pharmacokinetic model in accordance with at least one selectable pharmacokinetic parameter that controls the activity of the pharmacokinetic model within the phantom model over simulated time.

11. The simulator system according to claim 10, wherein the pharmacokinetic model models at least one pharmacokinetic substance, individual pharmacokinetic substances having a modeled imaging probe combined with a modeled radioisotope; and the at least one selectable pharmacokinetic parameter includes selection of the at least one pharmacokinetic substance included in the pharmacokinetic model and further includes selectable parameters for individual pharmacokinetic substances selected from the group consisting of introduction time for the individual pharmacokinetic substance into the phantom model, half-life of the radioisotope, gamma yield of the radioisotope, factors which influence the rate at which the imaging probe is processed by tissues modeled in the phantom model, monoclonal antibodies included in the imaging probe, diffusion rate of the imaging probe, clearance rate of the imaging probe from background tissue modeled in the phantom model, where the background tissue is tissue not targeted by the imaging probe, binding affinities for a specific target modeled in the phantom model, dosage of the radioisotope and dosage of the imaging probe.

12. The simulator system according to claim 1, wherein the dynamic integration module comprises a curve generator module for generating at least one time activity curve indicative of the activity of the pharmacokinetic model integrated with the phantom model.

13. The simulator system according to claim 12, wherein the dynamic integration module further comprises a conversion module for converting the at least one time activity curve to a set of discrete values, wherein the dynamic phantom data includes the set of discrete values.

14. A method for simulating a nuclear imaging process comprising the steps of:
providing for receiving of a digital phantom model and a digital pharmacokinetic model;
providing for integration of the pharmacokinetic model with the phantom model to generate dynamic phantom data representing activity of the pharmacokinetic model within the phantom model over simulated time;
providing for generation of a digital imager model representing a nuclear imager in accordance with at least one selectable imager parameter, wherein the at least one imager parameter controls activity of the imager model relative to simulated time;
providing for processing of the dynamic phantom data with the imager model for simulating at least one imaging process of the dynamic phantom data in accordance with the at least one imager parameter;
providing for generation of respective simulated sensed data in accordance with individual imaging processes of the at least one imaging process;
providing for receiving image data associated with the respective simulated sensed data and generating an image quality metric indicative of quality of the associated image data based on an analysis selected from the group consisting of a qualitative analysis and a quantitative analysis; and
providing for generation of feedback data of at least one adjusted parameter for selecting at least one imager parameter, at least one pharmacokinetic model, at least one phantom model, or combinations thereof, for use with at least one future imaging process in accordance with the image quality metric.

15. The method according to claim 14, wherein the at least one imager parameter is selected from the group consisting of simulated acquisition wait time and simulated acquisition duration time associated with individual imaging processes.

16. The method according to claim 15, further comprising the step of initiating the individual imaging processes at the selected simulated acquisition wait time.

17. The method according to claim 15, further comprising the step of continuing the individual imaging processes for the duration of the selected simulated acquisition duration time.

18. The method according to claim 14, further comprising the step of providing for generation of the phantom model in accordance with at least one selectable phantom parameter.

19. The method according to claim 14, further comprising the step of providing for generation of the pharmacokinetic model in accordance with at least one selectable pharmacokinetic parameter that controls the activity of the pharmacokinetic model within the phantom model over simulated time.

20. The method according to claim 19, wherein the pharmacokinetic model models at least one pharmacokinetic substance, individual pharmacokinetic substances having a modeled imaging probe combined with a modeled radioisotope; and the at least one selectable pharmacokinetic parameter includes selection of the at least one pharmacokinetic substance included in the pharmacokinetic model and further includes selectable parameters for individual pharmacokinetic substances selected from the group consisting of introduction time for the individual pharmacokinetic substance into the phantom model, half-life of the radioisotope, gamma yield of the radioisotope, factors which influence the rate at which the imaging probe is processed by tissues modeled in the phantom model, monoclonal antibodies included in the imaging probe, diffusion rate of the imaging probe, clearance rate of the imaging probe from background tissue modeled in the phantom model, where the background tissue is tissue not targeted by the imaging probe, binding affinities for a specific target modeled in the phantom model, dosage of the radioisotope and dosage of the imaging probe.

21. The method according to claim 14, further comprising the step of providing for generation of associated image data in accordance with the respective simulated sensed data.

22. The method according to claim 21, further comprising the steps of:
providing for provision of the image data associated with the respective simulated data to a display device for generating an associated image thereof.

23. The method according to claim 14, further comprising the step of providing for generation of the pharmacokinetic model in accordance with at least one selectable pharmacokinetic parameter that controls the activity of the pharmacokinetic model within the phantom model over simulated time, wherein the at least one adjusted parameter is generated for selecting a parameter selected from the group consisting of the at least one imager parameter and the at least one pharmacokinetic parameter for use with a future imaging process in accordance with the image quality metric.

24. The method according to claim 22, further comprising the step of providing for comparison of the image quality metric generated for an image or image data associated with simulated sensed data associated with respective at least first and second imaging processes, wherein the first and second imaging processes use different parameters selected from the group consisting of the at least one imager parameter and the at least one pharmacokinetic parameter.

25. The method according to claim 24, further comprising the step of providing for determination of the parameters used for the imaging process of the first and second imaging processes having an optimal image quality metric.

26. The method according to claim 14, further comprising the step of providing for generation of at least one time activity curve indicative of the activity of the pharmacokinetic model integrated with the phantom model.

27. The method according to claim 26, further comprising the step of providing for conversion of the at least one time activity curve to a set of discrete values, wherein the dynamic phantom data includes the set of discrete values.

28. A non-transitory computer readable medium storing a set of programmable instructions configured for execution by at least one processor for simulating a nuclear medicine imaging process, the programmable instructions comprising:

means for providing for receiving of a digital phantom model and a digital pharmacokinetic model;

means for providing for integration of the pharmacokinetic model with the phantom model to generate dynamic phantom data representing activity of the pharmacokinetic model within the phantom model over simulated time;

means for providing for generation of a digital imager model representing a nuclear imager in accordance with at least one selectable imager parameter, wherein the at least one imager parameter controls activity of the imager model relative to simulated time;

means for providing for processing of the dynamic phantom data with the imager model for simulating at least one imaging process of the dynamic phantom data in accordance with the at least one imager parameter; and means for providing for generation of respective simulated sensed data in accordance with individual imaging processes of the at least one imaging process;

means for providing for receiving image data associated with the respective simulated sensed data and generating an image quality metric indicative of quality of the associated image data based on an analysis selected from the group consisting of a qualitative analysis and a quantitative analysis; and means for providing for generation of at least one adjusted parameter for selecting at least one imager parameter, at least one pharmacokinetic model, at least one phantom model, or combinations thereof, for use with at least one future imaging process in accordance with the image quality metric.

* * * * *